US010220383B2

(12) United States Patent
Laukkonen et al.

(10) Patent No.: US 10,220,383 B2
(45) Date of Patent: Mar. 5, 2019

(54) SAMPLING AND ASSAY KIT, SAMPLE HOLDER AND METHOD

(71) Applicant: Orion Diagnostica OY, Espoo (FI)

(72) Inventors: Jukka Laukkonen, Espoo (FI); Jaana Raussi, Espoo (FI); Sanna Eilola, Espoo (FI); Jaakko Rissanen, Espoo (FI)

(73) Assignee: Orion Diagnostica OY, Espoo (FI)

( * ) Notice: Subject to any disclaimer, the term of this patent is extended or adjusted under 35 U.S.C. 154(b) by 27 days.

(21) Appl. No.: 15/312,580

(22) PCT Filed: May 12, 2015

(86) PCT No.: PCT/EP2015/060505
§ 371 (c)(1),
(2) Date: Nov. 18, 2016

(87) PCT Pub. No.: WO2015/177004
PCT Pub. Date: Nov. 26, 2015

(65) Prior Publication Data
US 2017/0087547 A1  Mar. 30, 2017

(30) Foreign Application Priority Data
May 21, 2014  (EP) ..................... 14169315

(51) Int. Cl.
*B01L 3/00*  (2006.01)
*A61B 5/15*  (2006.01)
(Continued)

(52) U.S. Cl.
CPC ........ *B01L 3/502* (2013.01); *A61B 5/150022* (2013.01); *A61B 5/150305* (2013.01);
(Continued)

(58) Field of Classification Search
CPC ........ A61B 5/150022; A61B 5/150305; A61B 5/150343; A61B 5/150351; A61B 5/150755; A61B 5/150908; B01L 2200/16; B01L 2300/047; B01L 2300/0609; B01L 2300/0838; B01L 2400/0406; B01L 3/502; B01L 3/5082; B01L 3/50825
See application file for complete search history.

(56) References Cited

U.S. PATENT DOCUMENTS 3,475,127 A   10/1969   Gilford
5,833,630 A   11/1998   Kloth
(Continued)

FOREIGN PATENT DOCUMENTS

CN   1728967 A   2/2006
CN   1929782 A   3/2007
(Continued)

*Primary Examiner* — Jennifer Wecker
(74) *Attorney, Agent, or Firm* — Norton Rose Fulbright US LLP

(57) ABSTRACT

A sampling and assay kit comprises a cuvette for holding a quantity of a buffer solution and a sample holder including a capillary tube for obtaining a sample. The sample holder includes a body portion which holds the capillary tube. The body portion when inserted in the cuvette, is effective to position the capillary tube within the cuvette at a predetermined position above the end of the cuvette.

10 Claims, 5 Drawing Sheets

(51) Int. Cl.
*G01N 33/50* (2006.01)
*C12M 3/00* (2006.01)
*B01L 3/14* (2006.01)
*A61B 10/00* (2006.01)

(52) U.S. Cl.
CPC .. *A61B 5/150343* (2013.01); *A61B 5/150351* (2013.01); *A61B 5/150755* (2013.01); *A61B 5/150908* (2013.01); *B01L 3/50825* (2013.01); *B01L 3/5082* (2013.01); *B01L 2200/16* (2013.01); *B01L 2300/047* (2013.01); *B01L 2300/0609* (2013.01); *B01L 2300/0838* (2013.01); *B01L 2400/0406* (2013.01)

(56) References Cited

U.S. PATENT DOCUMENTS

| | | | |
|---|---|---|---|
| 7,163,514 | B2 | 1/2007 | Zhou et al. |
| 7,378,054 | B2 | 5/2008 | Karmali |
| 8,574,496 | B2 | 11/2013 | Ruhl et al. |
| 2007/0131612 | A1 | 6/2007 | Duffy et al. |
| 2008/0193926 | A1 | 8/2008 | Abraham-Fuchs et al. |
| 2008/0260581 | A1 | 10/2008 | Rosman et al. |
| 2010/0255460 | A1* | 10/2010 | Kriz .................. B01L 3/50825 435/5 |
| 2010/0255609 | A1* | 10/2010 | Rutter .................. B01L 3/5023 436/518 |
| 2011/0020195 | A1* | 1/2011 | Luotola .............. A61B 10/0045 422/512 |
| 2011/0118626 | A1* | 5/2011 | Ragin ................ A61B 10/0291 600/573 |
| 2012/0214251 | A1 | 8/2012 | Bonecker |
| 2013/0065245 | A1 | 3/2013 | Rutter et al. |
| 2013/0302219 | A1 | 11/2013 | Li et al. |
| 2015/0285741 | A1* | 10/2015 | Bonecker ................ B01L 3/502 436/166 |
| 2017/0087547 | A1 | 3/2017 | Laukkonen et al. |

FOREIGN PATENT DOCUMENTS

| | | |
|---|---|---|
| CN | 1969184 A | 5/2007 |
| EP | 0638803 A1 | 2/1995 |
| EP | 0859664 B1 | 3/2003 |
| EP | 1366715 A1 | 12/2003 |
| EP | 1628770 B1 | 6/2008 |
| JP | S58-169553 A | 10/1983 |
| JP | H05-025358 A | 2/1993 |
| JP | 2000-501191 A | 2/2000 |
| JP | 2004-138502 A | 5/2004 |
| JP | 2010-513900 A | 4/2010 |
| RU | 2095787 C1 | 11/1997 |
| WO | 97/48492 A1 | 12/1997 |
| WO | 2005/071388 A1 | 8/2005 |
| WO | 2008/075044 A2 | 6/2008 |
| WO | 2009/118444 A1 | 10/2009 |
| WO | 2014/072170 A1 | 5/2014 |

* cited by examiner

SAMPLING AND ASSAY KIT, SAMPLE HOLDER AND METHOD

CROSS REFERENCE TO RELATED APPLICATIONS

This application is a national phase application under 35 U.S.C. § 371 that claims priority to International Application No. PCT/EP2015/060505 filed May 12, 2015, which claims priority to European Patent Application No. 14169315.0 filed May 21, 2014, all of which are incorporated herein by reference in their entirety.

This invention relates to sampling and assay kits, sample holders for use in such kits and methods of use of such kits. The invention has particular, although not exclusive, relevance to sample holders and sampling and assay kits, for use in clinical tests on biological fluids, such as blood.

In such tests, the biological fluid is collected and typically mixed with a reagent and a buffer. The reagent might be in liquid or solid form. A quantitative assay of the biological sample and reagent within the buffer typically utilises an analyser equipment using optical measurement techniques, in which a light beam or laser beam is directed through the mixture and a signal indicative of the optical properties of the sample, such as absorbance, reflectance, fluorescence, phosphorescence, luminescence and so on, is obtained.

In such quantitative assay techniques, it is necessary for the biological sample which has been freshly obtained, usually by a clinician, to be mixed with the reagent and the buffer in very accurate proportions. In order to provide such accurate proportions, it is known to provide sampling and assay kits which already include premeasured amounts of the reagent and the buffer.

One such test kit is disclosed in European patent specification EP 0859664. This document discloses a sampling and assay kit. In such an assay kit the biological sample is obtained by a capillary, which is discharged to a buffer present in a measuring cuvette by a plunger of the capillary. The measuring cuvette is closed with a cuvette closure device including a body part which has a sealed reagent storage chamber in a space between the lid of the body part and the plunger. A pre-measured amount of a reagent is stored in a reagent storage chamber of the closure device. Pressure by an operator, depresses the plunger of the device, so as to force a lower lid of the closure device to open, enabling discharge of the reagent into the buffer present in the cuvette.

An alternative arrangement is disclosed in WO 2005/071388, which discloses a sampling and assay device comprising at least three chamber portions, connected together in a row. One end chamber is capable of receiving a biological sample. The middle chamber contains reagent for forming the assay. A final portion of the device comprises a reaction chamber, including a buffer. The reaction chamber is inserted into an assay device, to enable an optical analysis of the enclosed buffer, reagent and biological sample to be performed.

WO 2009/118444 discloses an assay device, comprising a container including a sealed chamber, bounded on at least one side by a penetrable member. A sampler having a capillary passage for receiving the biological sample is provided, the sampler having a means configured to penetrate the penetrable member, to enable passage of the biological sample into the sealed chamber.

U.S. Pat. No. 5,833,630 discloses a sample collection device comprising a capillary holder for holding a blood sample, the capillary holder being insertable within a cuvette containing a reagent liquid. A pressure cap may be used to cause the capillary holder to be pushed into the cuvette.

US 2012/21451 discloses a test set for a photometric measuring device, where sample-taking device is integrated on a dosing container which may be inserted in a sealing manner into a filling opening of a mixing container.

US 2013/0302219 discloses devices for collection and elution of oral fluid samples by using a handle having a collection pad which is inserted into a collection tube. There is an adaptor in the collection tube with a narrowed portion for wringing a sample from the pad.

U.S. Pat. No. 3,475,127 discloses a sample measuring device for measuring precise volumes of fluid samples. A blood sample is collected within a capillary tube, the tube being provided with scored notches or grooves. The capillary tube is broken along a score line and the blood filled segment of the capillary tube is placed in a vessel including a reagent for analysis.

US 2008/0193926 discloses a device for extracting a smear sample. The smear sample is carried to a cavity with a sample carrier. A cotton swab may be used to introduce the sample to the cavity and then the cotton swab may be broken.

Such known sampling and assay kits, have the disadvantage that sample collection, transfer and mix with a reagent buffer might be difficult for a time pressured clinician. It is an object of the present invention, to provide a sampling and assay kit, a method of use of such a kit and the use of a sample holder in such a kit which address easier and quicker sample collection, transfer and mix with a reagent buffer.

According to a first aspect of the present invention there is provided a sampling and assay kit comprising:
a receptacle for holding a quantity of a liquid and a sample holder;
the sample holder comprising:
a sampler; and
a body portion, which holds the sampler and is insertable within the receptacle, the body portion including projection means;
wherein the receptacle has an internal projection such that when the body portion is inserted in the receptacle, the projection means of the body portion rests on said internal projection, so as to cause positioning of the sampler within the receptacle at a predetermined position above the end of the receptacle.

According to a second aspect of the present invention there is provided a method for analysing the amount of an analyte using a sampler held within a body portion connected with a weakened portion to a handle portion, the method including the steps of:
collecting a sample with the sampler;
inserting the sampler in a receptacle holding a liquid and allowing the sample to dilute from the sampler into liquid present in the receptacle;
removing a handle portion from the body portion;
inserting a stopper in the receptacle;
and measuring the amount of analyte in the sample.

According to a third aspect of the present invention there is provided a use of a sample holder in a sampling and assay kit comprising a receptacle for holding a quantity of a liquid and the sample holder;
the sample holder comprising:
a sampler; and
a body portion, which holds the sampler, the body portion being insertable within the receptacle;
the body portion including a projection means which, when the body portion is inserted in the receptacle, is effective to rest on an internal projection in the receptacle so as to position the sampler within the receptacle, at a predetermined position from the end of the receptacle.

Preferably the sampling and assay kit further comprises a stopper for the kit, the stopper including a plunger device effective to open a reagent chamber, said body portion including an indented portion which enables opening of the reagent chamber to enable ejection of reagent held within the reagent chamber into the receptacle when the stopper is inserted in the receptacle.

By such an arrangement, predetermined quantities of the components forming the sample to be analysed may be provided.

A sampling and assay kit, a method and a sample holder in accordance with embodiments of the invention, will now be described by way of example only, with reference to the accompanying drawings in which.

Figures 1, 2:
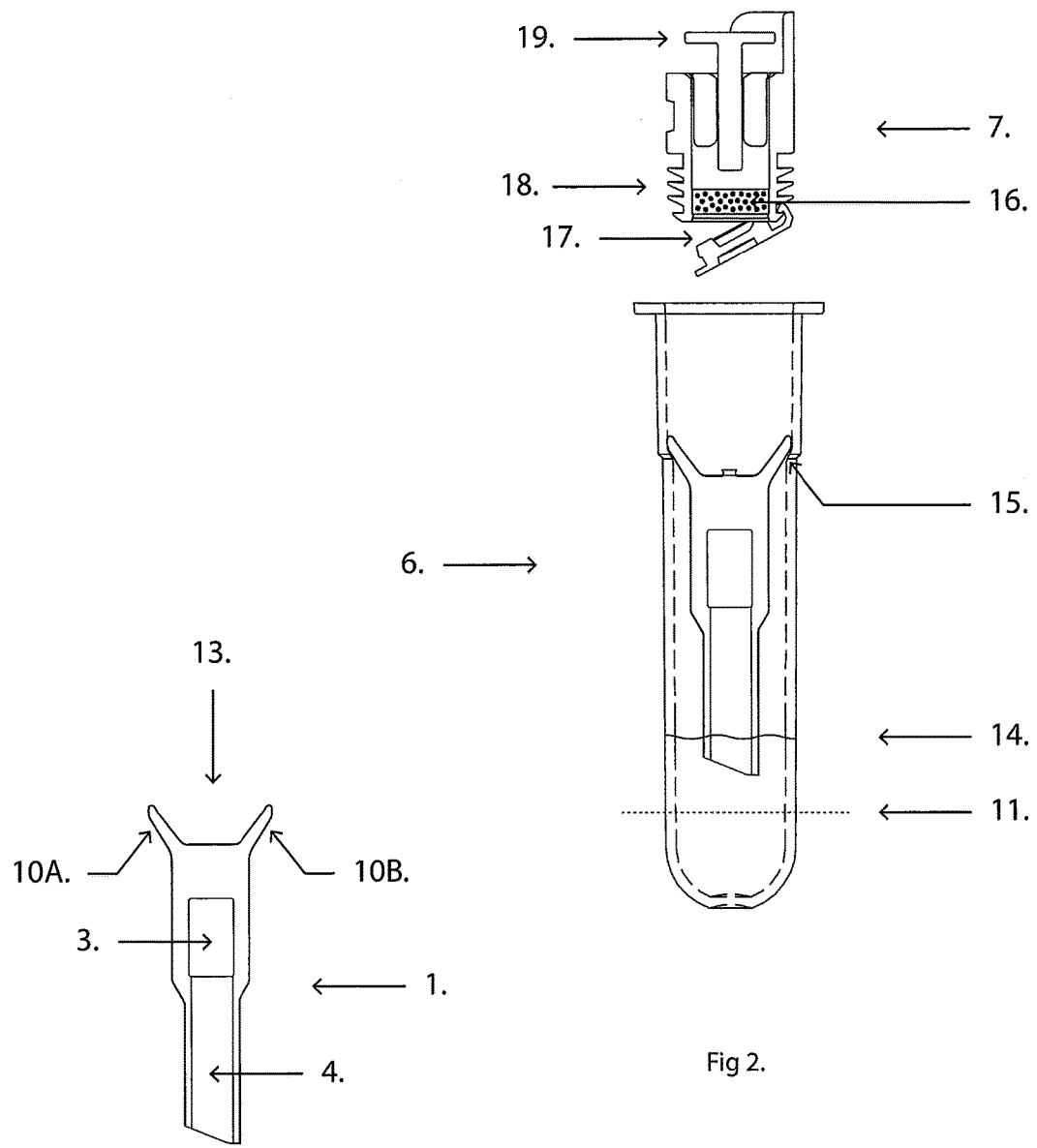
FIG. 1 is a schematic cross-section of a sample holder in accordance with a first embodiment of the invention, for use in a sampling and assay kit in accordance with the first embodiment.
FIG. 2 is a schematic cross-section of a cuvette holding the sample holder shown in FIG. 1, showing the insertion of a stopper.

Referring firstly to FIGS. 1 and 2 the first embodiment of an assay kit in accordance with the invention comprises three separate portions:

a sample holder 1 including a capillary tube 4;
a cuvette 6; and
a stopper 7.

Figure 3:
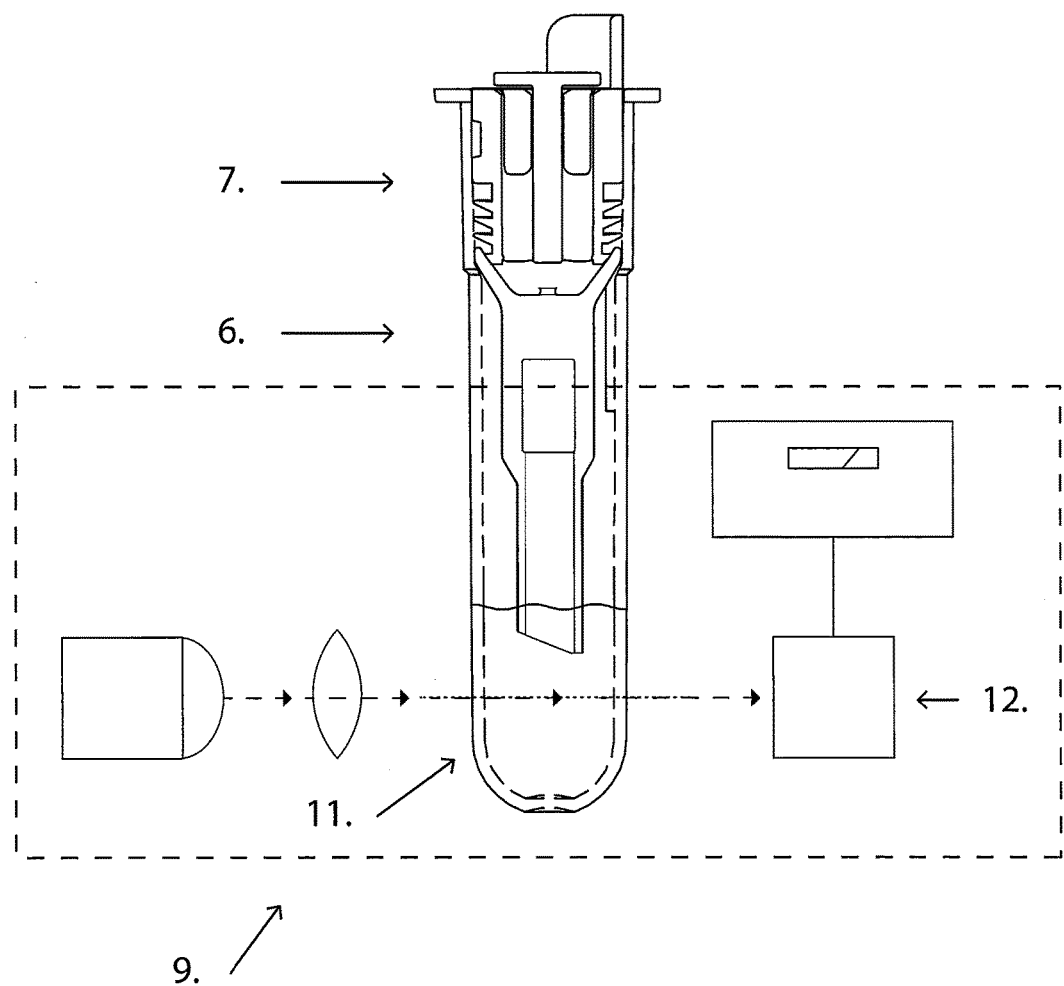
FIG. 3 is a schematic overview of the sampling and assay test kit of FIGS. 1 and 2, inserted in a test apparatus.

Referring now also to FIG. 3, in use of the sampling and assay kit, the sample holder 1 is placed in the cuvette 6, so that a sample within the capillary tube 4 is able to dilute to a liquid in the cuvette 6. Measurement of the sample is based on a photometric, preferably turbidometric method, as described in more detail later. Thus the cuvette 6 is inserted in a test apparatus 9 arranged to direct a beam of light, or radiation through the analyte present in the measuring zone 11 in the cuvette 6. The amount of light or radiation passing through the analyte is measured by a detector 12 and used to provide an analysis of the analyte.

The three portions of the assay kit will now be described in more detail.

Referring firstly particularly to FIG. 1, the sample holder 1 has a tubular body portion 3 in which the upper open end of capillary tube 4 is mounted. The top of the tubular body 3 is formed with two projections in the form of shoulders 10A, 10B whose function will be described hereafter, an indented area 13 being defined between the shoulders 10A, 10B. It will be appreciated that the capillary may be molded with the body part as a single part, as an alternative to being mounted in the body part.

Referring now particularly to FIG. 2, the lower part of this figure shows the sample holder 1 after it has been inserted in the cuvette 6. The cuvette 6 may be prefilled with a liquid 14 for diluting the sample from the capillary 4. This may be a buffer solution, for example and preferably will produce a clear solution in the cuvette 6 when mixed with the sample. The buffer solution may be any suitable buffer solution. Preferably, the buffer solution might be tris buffer or phosphate buffer. The buffer may contain some reagents, for example haemolysing compound.

The cuvette 6 has an inwardly facing ledge 15 on which, in use, the shoulder portions 10A, 10B of the body portion 3 of the sample holder 1 rest, so as to maintain the sample holder 1 accurately in position in the cuvette 6, with the end of the capillary tube 4 being positioned in the liquid 14 within the cuvette 6 to enable the sample to pass from the capillary 4 into the liquid 14, but with the capillary tube 4 being positioned above the measuring zone 11.

Referring now particularly to FIG. 2, and described in more detail in our previous application EP 0859664, the stopper 7 includes a chamber 16 in which a premeasured amount of a reagent may be stored, a lower lid 17, an externally threaded portion 18 and a plunger 19. The reagent may be of any suitable form, either liquid or solid. Examples of reagents are an analyte binding reagent (e.g. antibodies), solid particles, haemolysing compound (saponin) or red blood cells agglutinating compound (lectin).

Depression of the plunger 19 causes a downward movement of the lower lid 17, enabling ejection of the reagent stored in the chamber 16. FIG. 2 illustrates the lower lid 17 in an opened state outside the cuvette 6. When the stopper 7 is inserted into the cuvette 6, the externally threaded portion 18 of the stopper 7 acts as a seal and maintains the stopper 7 in place at the top of the cuvette 6.

The indented portion 13 of the sample holder 1 gives sufficient space within the cuvette 6 for the lower lid 17 of the stopper 7 to be opened within the cuvette 6 when the sample holder 1 is positioned within the cuvette 6. This enables the reagent stored in the compartment 16 to pass to the liquid 14 in the base of the cuvette 6.

As in use of the assay kit, the capillary tube 4 is held in place above the base of the cuvette 6, by the projections 10A, 10B of the sample holder resting on the inward facing ledge 15 of the cuvette 6, the capillary tube 4 is kept out of the light or radiation path through the cuvette 6. Thus, although the blood sample is able to pass into the buffer solution from the capillary tube 4, the presence of the capillary tube does not affect the optical measurement of the analyte in the measuring zone 11.

It will be appreciated that whilst in the embodiment described, the sample holder 1 has two projections in the form of shoulders 10A, 10B which rest on the inwardly formed ledge 15 in the cuvette 6, the sample holder 1 may have a different number of projections, or may be formed with a continuous projection which may rest on the ledge 15 in the cuvette 6.

Referring now to FIGS. 4 to 7, the second embodiment of an assay kit in accordance with the invention is an adaptation of the assay kit described in the first embodiment and thus corresponding features are correspondingly labelled.

Figures 4, 5:
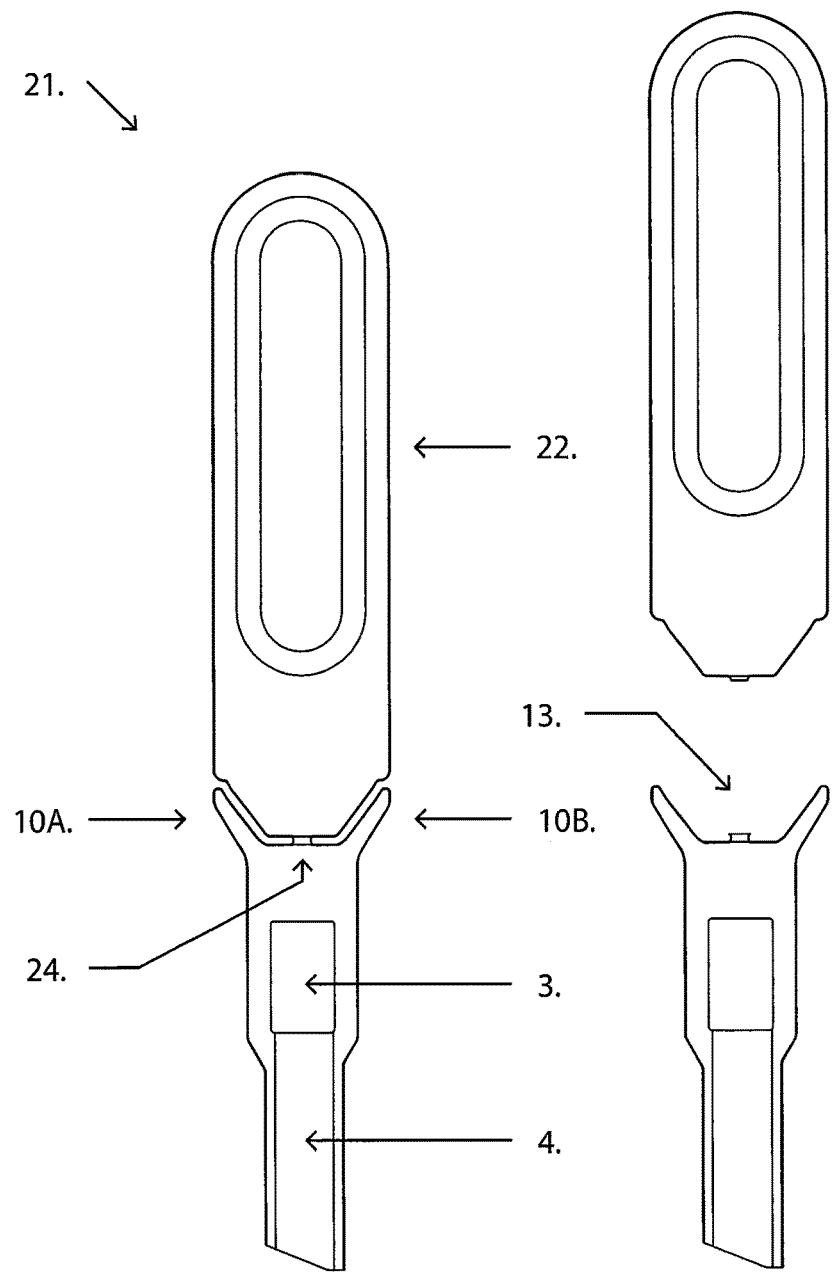
FIG. 4 is a schematic cross-section of a sample holder in accordance with the second embodiment of the invention for use in a sampling and assay kit in accordance with the second embodiment.
FIG. 5 shows the sample holder of FIG. 4, in which part of the handle has been separated from the rest of the sample holder.

However as shown in FIG. 4 the sample holder 21 in the second embodiment has a removable handle portion 22 which is attached, via a cylindrical spur 24, to the tubular body portion 3 in which the upper open end of capillary tube 4 is mounted. As in the first embodiment, the top of the tubular body 3 is formed with two projections in the form of shoulders 10A, 10B, with an indented area 13 being defined between the shoulders 10A, 10B.

The removable handle portion 22 is detachable from the rest of the sample holder 21 as indicated in FIG. 5. The detachment may be achieved by twisting the removable handle portion 22 at the cylindrical spur 24 to separate handle portion 22 from the body portion 3, so as to leave behind a stub on the intended area 13 on the body portion 3 as shown in FIG. 5.

Figure 6:
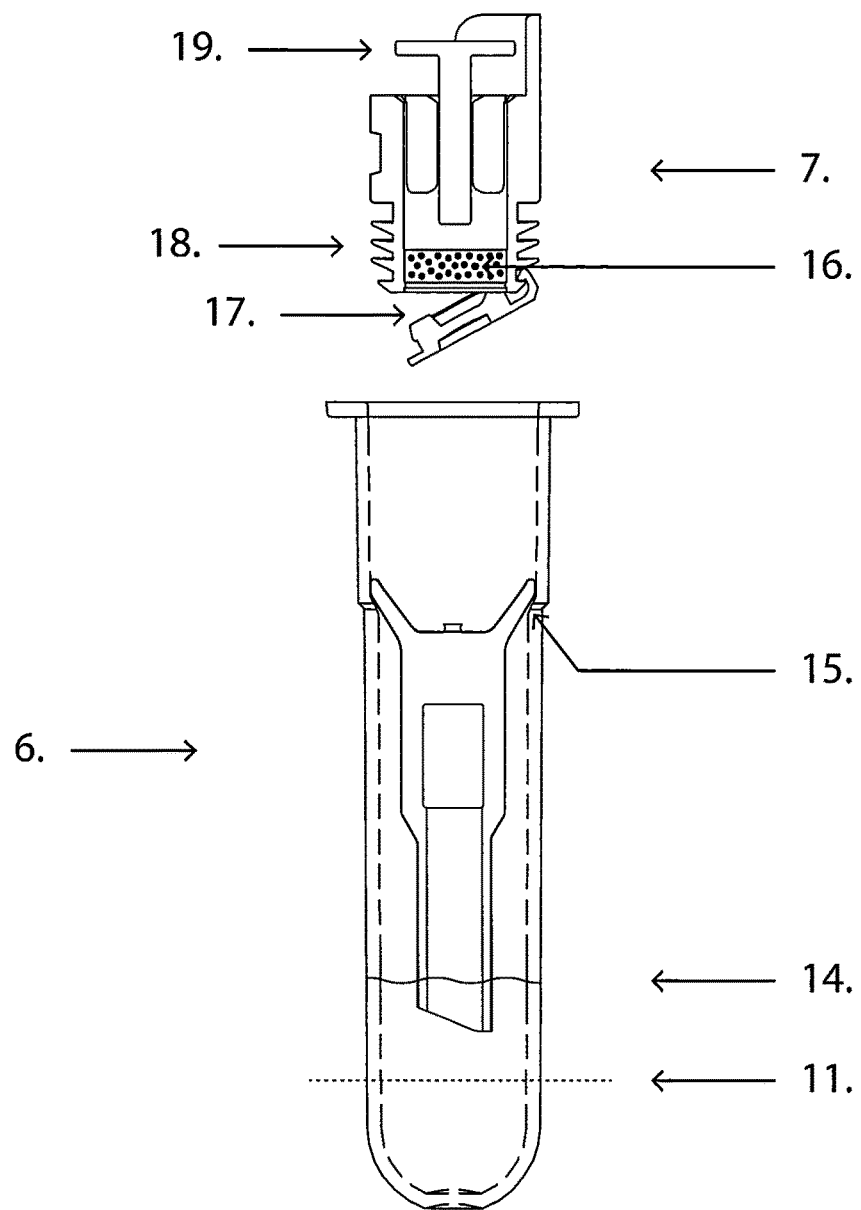
FIG. 6 is a schematic cross-section of a cuvette holding the sample holder shown in FIG. 5, showing the insertion of the stopper.

Referring now particularly to FIG. 6, the lower part of this figure shows the sample holder 21 after it has been inserted in the cuvette 6, with the removable handle portion 22 of the sample holder 21 removed as described above.

As in the first embodiment, the cuvette 6 has an inwardly facing ledge 15 on which, in use, the shoulder portions 10A, 10B of the body portion 3 of the sample holder 21 rest, so as to maintain the sample holder 21 accurately in position in the cuvette 6, with the end of the capillary tube 4 being positioned in the liquid 14 within the cuvette 6 to enable the sample to pass from the capillary 4 into the liquid 14, but with the capillary tube 4 being positioned above the measuring zone 11.

As in the first embodiment, depression of the plunger 19 causes a downward movement of the lower lid 17, enabling ejection of the reagent stored in the chamber 16. FIG. 6 illustrates the lower lid 17 in an opened state outside the cuvette 6, removal of the removable handle portion 22 from the rest of the sample holder 21 allowing the stopper 7 to be inserted in the cuvette 6 in the space above the tubular body part 3 of the sample holder 21 as shown in FIG. 6. As in the first embodiment, the stopper 7 is inserted into the cuvette 6, the externally threaded portion 18 of the stopper 7 acting as a seal and maintaining the stopper 7 in place at the top of the cuvette 6.

Figure 7:
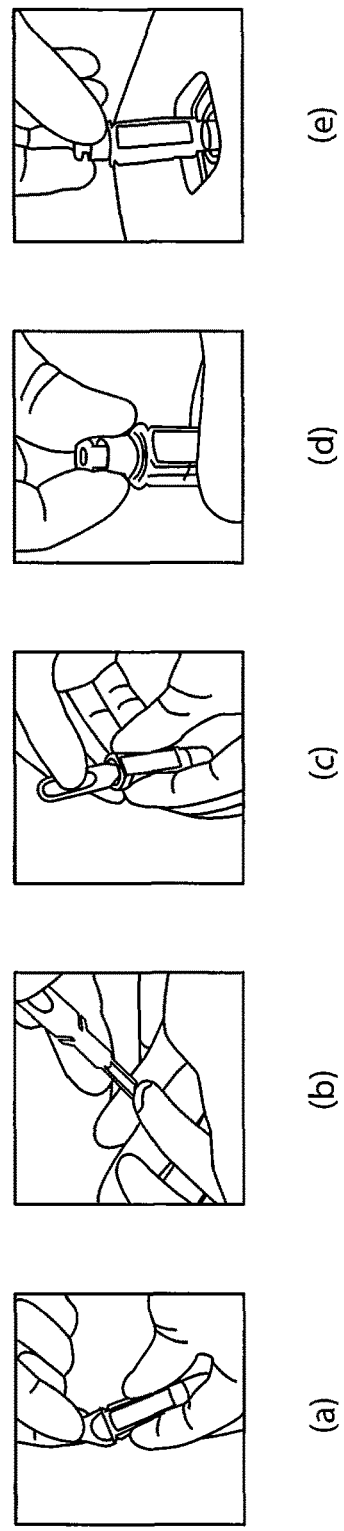
FIGS. 7(a)-7(e) are schematic presentations of the steps of a method of collecting and transferring a sample, in accordance with the second embodiment of the invention, using the sampling and assay kit shown in FIGS. 4 to 6.

Referring now to FIG. 7, this figure illustrates the use by a clinical operator, of the sample and assay kit in accordance with the second embodiment of the invention.

Referring firstly to FIG. 7(*a*), the clinical operative will remove a foil seal from the cuvette.

Referring now to FIG. 7(*b*), a blood sample is collected from a finger of a patient to the capillary 4 of the sample holder 21, by using the handle portion 22 to manipulate the capillary tube 4, without contaminating the sample. The blood sample will be drawn up the capillary tube 4 by capillary action.

Referring now to FIG. 7(*c*), the handle portion 22 may be used to transfer the sample holder 21 into the cuvette 6, the sample holder 21 hanging within the cuvette 6 by the projections in the form of shoulder portions 10A, 10B of the sample holder 1 resting on the inward ledge 15 of the cuvette as described above. This allows the blood sample to pass from the capillary tube 4 into the liquid 14 present in the cuvette 6. By twisting the handle portion 22, the handle portion 22 of the sample holder 21 may be removed from the body portion 3 of the sample holder 21, as described above.

Referring now to FIG. 7(*d*) the stopper is placed in the cuvette 6, with the lower lid 17 of the stopper 7 in a closed state, so that the reagent enclosed within the chamber 16 in the stopper is maintained within the chamber 16.

Finally, referring to FIG. 7(*e*), the cuvette 6 including the sample holder 21 with the handle portion 22 removed and the stopper 7, is then placed into the test apparatus 9. The plunger 19 in the stopper 7 is pressed and the lower lid 17 of the stopper 7 is opened, allowing the reagent held in the chamber 16, to be released from the chamber 16, to pass the sample holder 21 and subsequently to pass into the base of the cuvette 6.

Thus the mixture in the base of the cuvette 6, that is in the measuring zone 11, may be measured optically as described above in relation to FIG. 3 and the presence, or concentration, of an analyte in the liquid at the base of the cuvette 6 determined, using for example spectrophotometry.

It will be appreciated that whilst the removable handle portion 22 and the tubular body portion 3 are connected by a cylindrical spur 5 in the second embodiment, other weakened portions between the handle portion 22 and tubular body portion 3 of the sample holder 21 may be provided to enable removal of the handle portion 22. Examples of such alternative arrangements include a perforated section of the sample holder 21.

It will be appreciated that the form of the handle portion 22 particularly enables easier handling of the sample holder 21 for sample collection. However, the sampling and assay kit may be used in other applications. Transfer of samples other than blood samples, for example from sample vials, or liquid transfer from for example reagent bottles comprising standard or reference solutions is also made easier.

Whilst the sample collecting device described in the above embodiments is a capillary tube 4, other sample collection arrangements are possible in a sample and assay kit in accordance with the invention, for example a swab. The capillary tube 4 maybe itself coated with a reagent, for example heparin.

It will be appreciated that the sample holder 1 or 21 and cuvette 6 may be provided as a kit. The kit may further include the stopper 7. Whilst it is advantageous to provide preloaded quantities of the buffer and reagent in the cuvette 6 and stopper 7, these may be provided separately.

The invention claimed is:

1. A sampling and assay kit comprising:
   (1) separate stopper,
   (2) a receptacle for holding a quantity of a liquid, and
   (3) a sample holder;
      wherein the sample holder comprises:
      (a) a sampler; and (b) a body portion, that holds the sampler and is insertable within the receptacle, wherein the body portion including comprises projection means;
      wherein the receptacle has an internal projection such that when the body portion is inserted in the receptacle, the projection means of the body portion rests on said internal projection, so as to cause positioning of the sampler within the receptacle at a predetermined position above the end of the receptacle,
      wherein the stopper comprises a chamber for holding a reagent, a lid, and a plunger device configured to open the lid, wherein said body portion comprises an indented portion that is configured to enable opening of the lid so as to enable ejection of reagent held within the chamber into the receptacle when the stopper is inserted in the receptacle in a space above the body portion.

2. A sampling and assay kit according to claim 1 wherein said predetermined position is such that part of the sampler is within said liquid, but above a measuring zone for performing an optical analysis of the contents of the receptacle.

3. A sampling and assay kit according to claim 1 wherein said sampler is a capillary tube.

4. A sampling and assay kit according to claim 1 wherein said receptacle comprises a cuvette.

5. A sampling and assay kit according to claim 1 wherein said liquid is a buffer solution.

6. A sampling and assay kit according to claim 1 wherein said sample is a blood sample.

7. A sampling and assay kit according to claim 1 wherein the sample holder further comprises a handle portion.

8. A sampling and assay kit according to claim 7 wherein the sample holder further comprises a weakened portion which connects the handle portion and the body portion so as to enable separation of the handle and body portions.

9. A method for analyzing the amount of an analyte using a sampler held within a body portion connected with a weakened portion to a handle portion, the method including comprising the steps of:
   collecting a sample with the sampler;
   inserting the sampler in a receptacle holding a liquid and allowing the sample to dilute from the sampler into liquid present in the receptacle;
   removing a handle portion from the body portion;
   inserting a stopper in the receptacle in a space above the body portion; and
   measuring the amount of analyte in the sample.

10. The use of a sample holder in a sampling and assay kit comprising a receptacle for holding a quantity of a liquid and the sample holder;
   the sample holder comprising:
      a sampler; and
      a body portion, which holds the sampler, the body portion being insertable within the receptacle;
      the body portion including a projection means which, when the body portion is inserted in the receptacle, is configured to rest on an internal projection in the receptacle so as to position the sampler within the receptacle, at a predetermined position from the end of the receptacle;
      and a separate stopper configured to be inserted into a space above the body portion.

* * * * *